(12) United States Patent
Christensen

(10) Patent No.: US 8,388,944 B2
(45) Date of Patent: Mar. 5, 2013

(54) INACTIVATING ORGANISMS USING CARBON DIOXIDE AT OR NEAR ITS SUPERCRITICAL PRESSURE AND TEMPERATURE CONDITIONS

(75) Inventor: Tim W. Christensen, Ithaca, NY (US)

(73) Assignee: Novasterilis Inc., Ithaca, NY (US)

( * ) Notice: Subject to any disclaimer, the term of this patent is extended or adjusted under 35 U.S.C. 154(b) by 301 days.

(21) Appl. No.: 12/888,933

(22) Filed: Sep. 23, 2010

(65) Prior Publication Data

US 2011/0014184 A1 Jan. 20, 2011

Related U.S. Application Data

(62) Division of application No. 12/480,107, filed on Jun. 8, 2009, now Pat. No. 7,919,096, which is a division of application No. 10/577,050, filed as application No. PCT/US2004/020152 on Jun. 23, 2004, now Pat. No. 7,560,113.

(60) Provisional application No. 60/480,406, filed on Jun. 23, 2003.

(51) Int. Cl.
*A61K 47/08* (2006.01)
*A61K 39/00* (2006.01)

(52) U.S. Cl. .................................. 424/93.1; 424/78.26

(58) Field of Classification Search ........................ None
See application file for complete search history.

(56) References Cited

U.S. PATENT DOCUMENTS

| | | |
|---|---|---|
| 4,681,839 A | 7/1987 | Swartz |
| 4,944,837 A | 7/1990 | Nishikawa et al. |
| 5,213,619 A | 5/1993 | Jackson et al. |
| 5,370,740 A | 12/1994 | Chao et al. |
| 5,851,483 A | 12/1998 | Nicolle et al. |
| 5,996,155 A | 12/1999 | Chao et al. |
| 6,149,864 A | 11/2000 | Dillow et al. |
| 6,506,213 B1 | 1/2003 | Mandel et al. |
| 6,518,307 B2 | 2/2003 | McKenzie et al. |
| 6,613,278 B1 | 9/2003 | Mills et al. |
| 6,716,457 B1 | 4/2004 | Eagles et al. |
| 7,108,832 B2 | 9/2006 | Christensen et al. |
| 7,160,492 B2 | 1/2007 | King |
| 2003/0027125 A1 | 2/2003 | Mills et al. |
| 2003/0072677 A1 | 4/2003 | Kafesjian et al. |
| 2004/0033269 A1 | 2/2004 | Hei et al. |
| 2004/0120852 A1 | 6/2004 | Kanno |
| 2010/0080790 A1 | 4/2010 | Matthews et al. |

FOREIGN PATENT DOCUMENTS

EP 1782839 5/2007

OTHER PUBLICATIONS

Akkus et al, "Fracture resistance of gamma radiation sterilized cortical bone allografts", Journal of Orthopaedic Research, 19, 2001, pp. 927-934.
Cornu et al, "Effect of Freeze-Drying and Gamma Irradiation on the Mechanical Properties of Human Cancellous Bone", Journal of Orthopaedic Research, vol. 18, No. 3, 2000, pp.
Duffy et al, "An Epidemic of Corneal Destruction Caused by Plasma Gas Sterilization", Arch. Ophthalmol., vol. 118, Sep. 2000, pp. 1167-1176.
Godette et al, "Biomechanical Effects of Gamma Irradiation on Fresh Frozen Allografts in Vivo", Orthopedics, vol. 19, No. 8, Aug. 1996, pp. 649-653.
Holyoak et al, "Toxic effects of ethylene oxide residuals on bovine embryos in vitro", Toxicology, 108, 1996, pp. 33-38.
Ikarashi et al, "Cytotoxicity of medical materials sterilized with vapour-phase hydrogen peroxide", Biomaterials, vol. 16, No. 3, 1995, pp. 177-183.
Jahan et al, "Long-Term Effects of Gamma-Sterialization on Degradation of Implant Materials", Appl. Radiat. Isot., vol. 46, No. 6/7, 1995, pp. 637-638.
Kamihira, et al. Sterilization of Microorganisms with Supercritical Carbon Dioxide. Agric. Biol Chem. 1987; 51(2): 407-412.
Lin, et al. Inactivation of *Saccharomyces cerevisiae* by Supercritical and Subcritical Carbon Dioxide. Biotechnol. Prog. 1992;8; 458-461.
Schiewe et al, "Toxicity Potential of Absorbed-Retained Ethylene Oxide Residues in Culture Dishes on Embryo Development in Vitro", Journal of Animal Science, vol. 60, No. 6, 1.
Windebank et al, "Residual Ethylene Oxide in Hollow Fiber Hemodialysis Units Is Neurotoxic in Vitro", Annals of Neurology, vol. 26, No. 1, Jul. 1989, pp. 63-68.

*Primary Examiner* — Bao Li
(74) *Attorney, Agent, or Firm* — Welsh Flaxman & Gitler LLC

(57) ABSTRACT

Whole organisms are inactivated by at least a factor of $10^6$ using carbon dioxide at or near its supercritical pressure and temperature conditions.

4 Claims, 3 Drawing Sheets

Untreated Bacteria

Treated Bacteria

Untreated Bacteria

Treated Bacteria

Untreated Bacteria

Treated Bacteria

INACTIVATING ORGANISMS USING CARBON DIOXIDE AT OR NEAR ITS SUPERCRITICAL PRESSURE AND TEMPERATURE CONDITIONS

CROSS REFERENCE TO RELATED APPLICATION

This application is a divisional of U.S. patent application Ser. No. 12/480,107, entitled, "INACTIVATING ORGANISMS USING CARBON DIOXIDE AT OR NEAR ITS SUPERCRITICAL PRESSURE AND TEMPERATURE CONDITIONS", filed Jun. 8, 2009 now U.S. Pat. No. 7,919,096, which is a divisional of U.S. patent application Ser. No. 10/577,050, entitled, "INACTIVATING ORGANISMS USING CARBON DIOXIDE AT OR NEAR ITS SUPERCRITICAL PRESSURE AND TEMPERATURE CONDITIONS", filed Sep. 19, 2006, now U.S. Patent No. 7,560,113, which is the National Stage of International Application No. PCT/US2004/020152, entitled "INACTIVATING ORGANISMS USING CARBON DIOXIDE AT OR NEAR ITS SUPERCRITICAL PRESSURE AND TEMPERATURE CONDITIONS", filed Jun. 23, 2004, which claims the benefit of U.S. Patent Application Ser. No. 60/480,406, filed Jun. 23, 2003, entitled, "METHODS FOR OBTAINING WHOLE-ORGANISM THERAPEUTIC AGENTS USING NEAR OR SUPERCRITICAL CARBON DIOXIDE", which is expired.

BACKGROUND OF THE INVENTION

1. Field of the Invention

The present invention relates to whole organisms which have been inactivated by at least $10^6$ using carbon dioxide at or near its supercritical pressure and temperature conditions, immunogenic compositions thereof, methods for preparation, and methods for immunization.

2. Description of the Related Art

Vaccines represent one of the seminal developments in our ongoing battle against disease. Vaccination is still the best defense against existing, novel, and manipulated pathogens. The earliest whole-cell vaccines were prepared by inactivating a given pathogen using chemical or heat processes. Whole-cell vaccines have significant advantages over attenuated and subunit vaccines. Chemical or thermal inactivation of the pathogen is simple and inexpensive, and provides rapid access to a vaccine. Both subunit vaccines and attenuated vaccines require considerable time and expense before they can be put to use. Despite the advantages of chemical inactivation, chemically inactivated vaccines sometimes fail to elicit robust and protective immune responses [2-4]. The addition of adjuvants to these preparations may boost the immune response, but immunity is still insufficient in many cases and may require frequent boosting.

Many complications associated with chemically inactivated vaccines arise from the simple fact that inactivation alters the chemical properties of key antigens required to elicit a protective immune response. The development of a rapid, inexpensive, and effective process to inactivate a pathogen while maintaining the integrity of its antigens would represent a powerful new tool in vaccine development.

Recent work has effectively demonstrated that microbes inactivated by a non-denaturing process do, in fact, elicit more robust immune responses than chemically inactivated pathogens [5]. "Ghosts" as they are known colloquially, are the empty shells of microbes that have been inactivated by the controlled expression of the PhiX174 lysis gene "E" [6]. Essentially the cytoplasmic contents of the cells are expelled via the transmembrane tunnel formed by the lysis protein [6]. Vaccines prepared through this genetic manipulation have been shown to be superior to chemically inactivated pathogens, most likely due to the non-denaturing inactivation procedure [3]. Moreover, it is hypothesized that the more robust immune response is not simply a function of individual proteins, but also is related to the route of antigen presentation.

Cell walls remain largely intact, native surface antigens are preserved, and bioadhesive properties are likely maintained in ghost vaccine preparations. All of these characteristics endow ghost vaccines with inherent adjuvant properties that contribute to protective immune responses [3, 7-17]. The usefulness of the bacterial ghost system is extended by inactivating bacteria expressing antigens that are derived from other pathogens. The end result is a vaccine with inherent adjuvant properties that is protective against any number of desired bacterial, viral, protozoan, and fungal pathogens [12, 13, 15, 16, 18]. There are concerns about the endotoxicity of lipid A and lipopolysaccharide (LPS) in these whole cell vaccines. However, it has been demonstrated that endotoxicity is not a real limit to the use of ghost vaccines [17].

Despite its promise, the ghost vaccine technology exhibits a number of drawbacks. The first of these concerns centers on safety. The phage lytic system employed typically results in only a 4-log reduction in colony forming units (CFU) [5]. The remaining organisms must be inactivated by further processing. This may or may not be the case. The ghost system uses an additional kill mechanism to inactivate the remaining survivors [5]. This layering of genetic systems in the ghost technology is a cause for additional concern. Because these genetic systems are maintained within the chosen cells by selection on various antibiotic containing media [19, 20], lateral transfer of antibiotic resistance to other pathogens within an individual is a possibility [21].

In addition to safety concerns, the ghost system only works with Gram-negative bacteria. Furthermore, genetic manipulation of additional serotypes may be required to generate a broadly protective vaccine. Therefore, the applicability of the ghost technology is limited to the gram-negative bacteria that are tractable to genetic manipulation. These limitations preclude a significant number of pathogens, notably: *Staphylococcus aureus, Staphylococcus epidermidis, Streptococcus pneumoniae, Streptococcus agalactiae, Streptococcus pyrogenes, Enterococcus* spp., *Bacillus anthracis, Bacillus cereus, Lactobacillus* spp., *Listeria monocytogenes, Nocardia* spp., *Rhodococcus equi, Erysipelothrix rhusiopathiae, Corynebacterium diptheriae, Propionibacterium acnes, Actinomyces* spp., *Clostridium botulinum, Clostridium difficile, Clostridium perfringens, Clostridium tetani,* and *Peptostreptococcus* spp. The applicability of ghost vaccine technologies is further limited by its failure to inactivate spores, which are insensitive to induction of lysis genes due to their dormant nature.

Whole-cell vaccines produced on the ghost vaccine technology are superior to chemically inactivated pathogens, but cannot be developed rapidly. Even if the microbe is previously known, considerable time and expense are required to generate a new ghost vaccine for a given pathogen, especially for novel or genetically intractable pathogens. The present invention does not require introduction of a phage lysis gene and induction of a lytic program.

The need for new and broadly applicable inactivation technologies is exacerbated by the very nature of biological weapons. The pathogens that are, or may be employed as bio-warfare and bio-terror agents such as Anthrax, Tularemia, Botulism, Plague, Epsilon toxin, Q fever, enterotoxin B, Typhus fever, Melioidosis, and Brucellosis are not usually endemic diseases in humans. As such there is very little, if any, commercial advantage to generating vaccines using expensive and time-consuming techniques. An appealing alternative that would speed the production of such vaccines and enable quick response to emerging serotypes is an inactivation technology that in and of itself generates high quality vaccines. Bacterial inactivation by supercritical $CO_2$ represents such a technology. The technology for using supercritical $CO_2$ is well-known and has been adapted to large industrial applications, including the extraction of natural compounds from plant materials [22] and detoxification of contaminated soil [23]. Supercritical $CO_2$ applications have also found their way into medical circles as a process for bone de-lipidation [24], drug manufacture [25], and sterilization among others [1]. The first attempts to use supercritical $CO_2$ as a sterilant resulted in inadequate levels of inactivation [26].

Recently, in U.S. Pat. No. 6,149,864 to Dillow et al. (the entire content of which is expressly incorporated hereinto by reference), the use of supercritical $CO_2$ was disclosed as an alternative to existing technologies for sterilizing a wide range of products for the healthcare industry with little or no adverse effects on the material treated. Specifically, the Dillow '864 patent disclosed the inactivation of a wide range of vegetative microbial cells using supercritical carbon dioxide with agitation and pressure cycling. However, only one spore-forming bacterium was investigated in the Dillow '864 patent, specifically, *B. cereus*. No disclosure appears in Dillow '864 patent regarding the efficacy of the therein suggested techniques using currently accepted bio-indicator standards used to judge sterilization (i.e., *B. stearothermophilus* and *B. subtilis*). Subsequently, however, other investigators achieved only a 3.5-log reduction in *B. subtilis* spore forms using the process disclosed in the Dillow '864 patent [27].

In addition to bacterial inactivation, viral inactivation is realized using supercritical $CO_2$ [28]. Moreover it has been shown that sterilization by supercritical $CO_2$ does not affect the properties of a biodegradable polymer (PLGA) and leaves bacterial cells intact [1].

It would therefore be desirable if processes could be provided whereby organisms are inactivated utilizing near or supercritical $CO_2$ for the purpose of generating whole-cell therapeutic agents. It is towards fulfilling such a need that the present invention is directed.

SUMMARY OF THE INVENTION

In general, the methods of the present invention result in whole-organism therapeutic agents by treatment of the organisms using near or supercritical carbon dioxide. In preferred embodiments, methods of this invention treat organisms with near or supercritical carbon dioxide at pressures between about 1000 psi to about 3500 psi, at temperatures in the range of between about 25° C. to about 60° C., and times ranging from about 10 minutes to about 12 hours. In especially preferred embodiments, the present invention utilizes the techniques disclosed in commonly owned Int'l Patent Application Serial No. PCT/US2004/020152, filed on Jun. 17, 2004, the entire content of which is expressly incorporated hereinto by reference.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
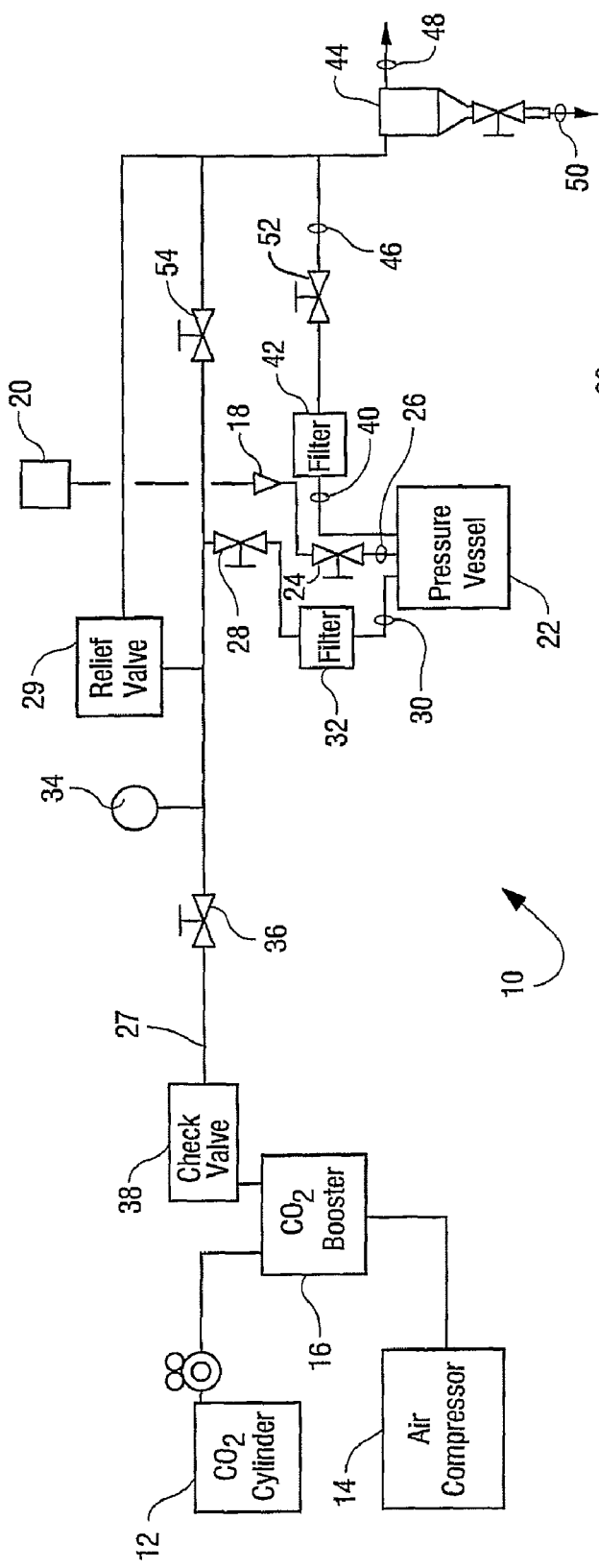
FIG. 1 is a schematic view of a presently preferred apparatus used for inactivation.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

As noted previously, the present invention results in the inactivation of organisms for the purposes of generating whole-cell therapeutic agents. Most preferably, the carbon dioxide is at or near its supercritical pressures and temperature conditions. Thus, inactivation by the present invention may be achieved using carbon dioxide at (i) a pressure from about 1000 psi to about 3500 psi and (ii) a temperature from about 25° C. to about 60° C. Most preferably, carbon dioxide is held at or near its supercritical pressure and temperature conditions for a time from about 20 minutes to about 12 hours. The carbon dioxide employed in the practice of the present invention is most preferably substantially pure. Thus, trace amounts of other gases may be tolerated provided that the ability of carbon dioxide to inactivate whole organisms is not impaired. For ease of further discussion below, the term "supercritical carbon dioxide" will be used, but it will be understood that such a term is non-limiting in that carbon dioxide within the pressure and temperature ranges as noted immediately above may be employed satisfactorily in the practice of the present invention.

Therapeutic agents such as immunogenic preparations of whole organisms (or vaccines comprised thereof) prepared by the process of the present invention may be used for immunization and/or vaccination. The former requires that an immune response specific for the organism be induced after administration to a subject in need thereof (e.g., antibodies, B or T lymphocytes specific for one or more antigens of the organism) while the latter provides an immune response which is prophylactic (i.e., treatment prior to infection by a pathogenic organism) or therapeutic (i.e., treatment subsequent to infection by a pathogenic organism). The invention involves contacting live organisms with supercritical carbon dioxide such that they are inactivated by a factor of at least about $10^6$, at least about $10^7$, or at least about $10^8$ without substantial loss of whole cells. The resultant composition may be comprised of at least about $10^5$, at least about $10^6$, at least about $10^7$ or least about $10^8$ whole organisms; alternatively, the concentration may be at least about $10^5$, at least about $10^6$, at least about $10^7$, or at least about $10^8$ whole organisms per milliliter. The amount of protein (e.g., native antigen) of the organisms may be at least about 10 ng, at least about 100 ng, at least about 1 μg, or at least about 10 μg.

A wide range of organisms can be inactivated using the present invention, including for example, gram-positive bacteria, gram-negative bacteria, viruses, fungi, protozoa, and helminths. Infections which are enteric, fungal, herpesvirus, parasitic, respiratory, and vector-borne; sexually-transmitted diseases; and viral hepatitis may be treated. Given the low temperatures and low pressures, inactivation by supercritical carbon dioxide using the process of the present invention is especially useful to produce whole-cell therapeutic agents (e.g., immunogens and vaccines) while maintaining the properties of thermally-labile and/or hydrolytically-labile antigens of the organisms. Spore and/or vegetative forms resistant to phage lysis may be efficiently inactivated. Organisms do not have to be genetically manipulated to inactivate or attenuate them. They may be grown in culture medium or a permissive host in the indicated amount and then inactivated. Inactivation by supercritical carbon dioxide results in at least a $10^6$ reduction in viability or infectivity (i.e., organisms are killed) with most of the organisms having intact cell walls (e.g., at least about $10^5$, at least about $10^6$, at least about $10^7$, or least about $10^8$ intact whole organisms). Viability may be determined by growth in culture (e.g., number of colonies or plaques) or infection of susceptible hosts (e.g., morbidity or mortality of immunized subjects vs. a naive control population). This allows prompt development of vaccine candidates for novel pathogens and emergent diseases, which may be evaluated in animals and tried in humans.

Organisms which may be inactivated include but are not limited to: *Actinomyces* spp., *Bacillus anthracis, Bacillus cereus, Bordetella pertussis, Campylobacter* spp., *Corynebacterium diptheriae, Clostridium botulinum, Clostridium difficile, Clostridium perfringens, Clostridium tetani, Corynebacterium diptheriae, Enterococcus* spp., *Erysipelothrix rhusiopathiae, Escherichia coli, Haemophilus influenza, Heliobacter pylori, Listeria monocytogenes, Mycoplasma pneumoniae, Neisseria meningitidis, Nocardia* spp., *Pseudomonas aeruginosa, Propionibacterium acnes, Rhodococcus equi, Staphylococcus aureus, Staphylococcus epidermidis, Streptococcus agalactiae, Streptococcus pneumoniae, Streptococcus pyrogenes,* and *Vibrio cholerae;* cytomegaloviruses, enteric viruses, Epstein-Barr viruses, hepatitis viruses, herpesviruses, influenza viruses, papillomaviruses, parainfluenza viruses, poliovirus, respiratory syncytial virus, rubella virus, smallpox virus, and varicella virus; fungi causing blastomycosis, candidiasis, coccidioidomycosis, cryptococcosis, histoplasmosis, paracoccidioidomycosis, or pythiosis; and parasites causing leprosy, malaria, or schistosomiasis. A combination of two or more different organisms (e.g., DPT vaccine) may be used. The transmission of vector-borne disease may be interrupted by immunization of animal intermediaries. Animals may be immunized to produce antibodies for passive immunization of a human subject or binding agents for immunoassays.

A subject may be immunized (this may include vaccination in cases where a prophylactic and/or therapeutic effect is achieved) one or multiple times, and with or without other organisms inactivated by other processes (e.g., formalin inactivation), attenuated organisms, or acellular (e.g., one or more purified antigens alone) preparations. The amount of immunogen (or vaccine) administered to a subject in need of therapy or prophylaxis, as well as its extent, is effective in treatment of the subject at risk for or affected by an infectious disease. The subject may be any animal or human. Mammals, especially humans and rodent or primate models of disease, may be treated. Thus, both veterinary and medical methods are contemplated. The preparation may be used as primary and/or secondary immunogen (or vaccine) at suitable intervals (e.g., several weeks or months between doses).

Suitable choices in amounts and timing of doses, formulation, and routes of administration can be made with the goals of achieving a favorable response in the subject afflicted by an infectious disease or at risk thereof (i.e., efficacy), and avoiding undue toxicity or other harm thereto (i.e., safety). A single dose may range between 0.1 mL and 1.0 mL of an immunogenic preparation containing protein of the organisms from about 10 ng/mL to about 10 μg/mL. The route of administration may be enteral, mucosal, parenteral, or topical; it may be adsorbed, ingested, inhaled, or injected. For organism-specific antigens (e.g., at least two, at least five, or at least ten different native antigens) in the composition, labile epitopes of the antigens which are dependent on their conformation for immunologic activity (i.e., immunogenicity) may be retained instead of being denatured by chemical (e.g., formalin) or physical (e.g., heat) inactivation.

Therefore, "effective" refers to such choices that involve routine manipulation of conditions to achieve a desired effect. It will also be understood that the specific dose level to be achieved for any particular subject may depend on a variety of factors, including age, gender, health, medical history, weight, combination with one or more other drugs, and severity of disease. The term "treatment" of an infectious disease refers to, inter alia, reducing or alleviating one or more symptoms in a subject, preventing one or more symptoms from worsening or progressing, promoting recovery or improving prognosis, and/or preventing disease in a subject who is free therefrom as well as slowing or reducing progression of existing disease. For a subject, improvement in a symptom, its worsening, regression, or progression may be determined by an objective or subjective measure. Efficacy of treatment may be measured as an improvement in morbidity or mortality (e.g., lengthening of survival curve for a selected population). Prophylactic methods (e.g., preventing or reducing the incidence of relapse) are also considered treatment. Treatment may also involve combination with other existing modes of treatment (e.g., antibiotics, antivirals, passive immunization with antitoxin or hyperimmune antibodies). Thus, combination treatment with one or more other drugs and one or more other medical procedures may be practiced. The amount of immunogen (or vaccine) which is administered to a subject is preferably an amount that does not induce toxic or other deleterious effects which outweigh the advantages which result from its administration. Further objectives are to reduce in number, diminish in severity, and/or otherwise relieve suffering from the symptoms of the infection as compared to recognized standards of care.

Medicaments or pharmaceutical/diagnostic compositions may be prepared from the inactivated organisms. Use of preparations which further comprise a pharmaceutically acceptable carrier and/or other components useful for delivering immunogen to a subject are known in the art. Addition of such carriers and other components (e.g., adjuvants, antibiotics, preservatives, stabilizers) to the preparation is well within the level of skill in this art. Adjuvants such as aluminum or calcium gels, bacterial toxins, cytokines, genes encoding cytokines, muramyl peptides, and saponins may be included to enhance the immune response to antigen. Antibiotics include amphotericin B, chlortetracycline, gentamycin, kanamycin, neomycin, polymyxin B, and streptomycin to prevent bacterial contamination of the composition and/or to treat bacterial infection of the treated subject (e.g., at the same or different time as immunization with the preparation of the present invention). Preservatives include benzethonium chloride, ethylenediamine-tetraacetic acid sodium, 2-phenoxyethanol, and sodium bisulfite (formaldehyde is preferably not included). Stabilizers include albumin, gelatin, glutamate salts, glycine, lactose, sorbitol, sucrose, and trehalose. Antibodies (e.g., hyperimmune or toxin specific) may be administered at the same or different time as the immunogenic preparation to provide passive immunization for a subject; such antibodies in the form of immune globulins may be made by immunizing an animal with the immunogenic preparation of the present invention or other preparations.

Given the existing literature and corollaries to the ghost technology for vaccine production, it is possible to generate some predictions about the properties of organisms inactivated by supercritical carbon dioxide as vaccines (Table 1).

TABLE 1

Comparison of Inactivation Technologies

| | Method of Inactivation | | |
|---|---|---|---|
| | Formalin | Ghost | Supercritical $CO_2$ |
| Speed of development | + | − | + |
| Non-denaturing | − | + | + |
| >6-Log inactivation | + | − | + |
| Inactivation: Gram negative bacteria | + | +/− | + |
| Gram positive bacteria | + | − | + |
| Viruses | + | − | + |
| Maintains structural properties of bacterium | − | + | + |
| Adjuvant properties | − | + | + |
| No toxic chemical residues | − | + | + |
| Lacks antibiotic resistance genes | + | − | + |

As noted previously, it is contemplated that contacting microorganisms with at least $CO_2$ at or near its supercritical pressure and temperature conditions and an optional chemical additive sufficient to inactivate the microorganisms and produce intact microbial cells and viruses when assayed by various methods including transmission and scanning electron microscopy.

Six-log ($10^6$) reductions in viability may be achieved in accordance with the present invention by subjecting microorganisms to temperature and pressure conditions using a chemical additive-containing supercritical carbon dioxide as a fluid, and especially where the fluid is agitated during the process. Organisms may be washed after inactivation and purified to remove the chemical additive to acceptable levels. The presence of trace amounts of chemical additive may be used to identify a whole organism preparation inactivated by the present invention.

The optional chemical additive used with supercritical carbon dioxide may be comprised of peroxides and/or carboxylic acids. Preferred carboxylic acids include alkanecarboxylic acids and alkanepercarboxylic acids, which may be optionally substituted at the alpha carbon with one or more electron-withdrawing substituents, such as halogen, oxygen and nitrogen groups. Particularly preferred species of chemical additives may be comprised of hydrogen peroxide ($H_2O_2$), acetic acid (AcA), peracetic acid (PAA), and trifluoroacetic acid (TFA), and mixtures thereof. One particularly preferred chemical additive that may be used is commercially available SPORECLENZ® sterilant which is a mixture of acetic acid, hydrogen peroxide, and peracetic acid.

The chemical additive may be used in an inactivation enhancing effective amount of at least about 0.001 vol. % and greater, based on the total volume of the carbon dioxide. The amount of chemical additive will be dependent upon the particular chemical additive that is used. Thus, for example, peracetic acid may be present in relatively small amounts of about 0.005 vol. % and greater, while acetic acid may need to be present in an amount of about 1.0 vol. % and greater. Thus, a range of at least about 0.001 vol. % and greater, up to about 2.0 vol. % will typically be needed in order to achieve an inactivation enhancing effect in combination with carbon dioxide.

Figure 2:
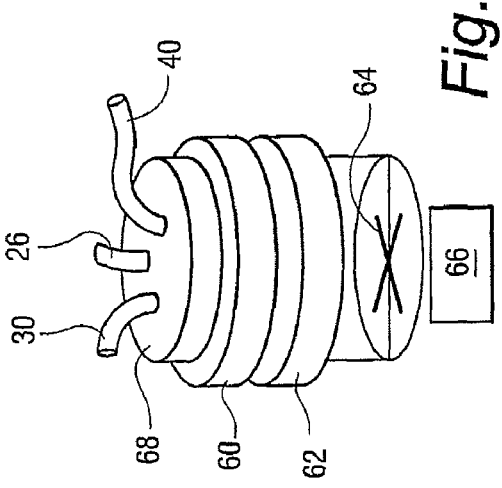
FIG. 2 is a detailed schematic view of the pressure vessel employed in the apparatus of FIG. 1.
Figure 3A:
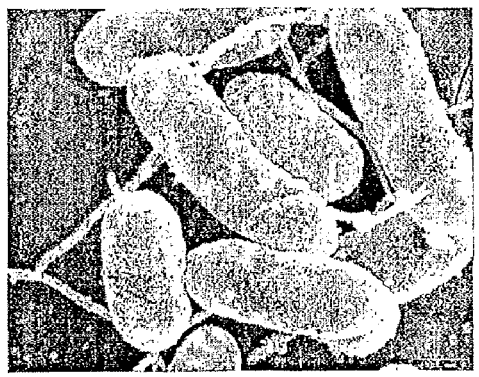
FIG. 3 shows inactivation of whole cells: scanning electron microscopy (SEM) shows untreated bacteria (FIGS. 3A-3C) and treated bacteria (FIGS. 3D-3F) have intact cell walls, protein extracts of untreated and treated bacteria were separated by molecular weight (cf. standards in marker lane) using one-dimensional polyacrylamide gel electrophoresis (PAGE) under denaturing conditions (FIG. 3G) and shows that total protein was substantially unchanged, and two-dimensional gel electrophoresis at higher resolution with isoelectric focusing under native conditions and separation by molecular weight under denaturing conditions for untreated bacteria (FIG. 3H) or treated bacteria (FIG. 3I) shows that proteins are substantially not denatured or lost by inactivation.
Figure 3D:
Figure 3B:
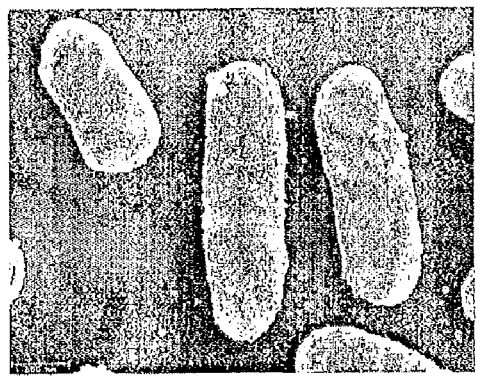
Figure 3E:
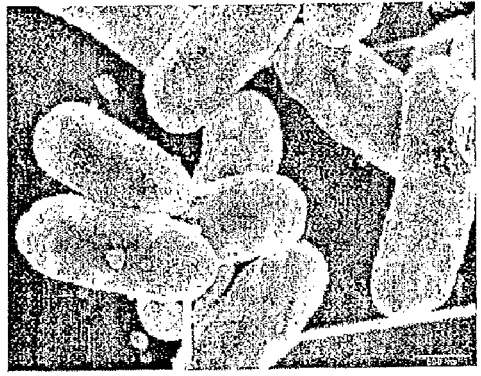
Figure 3C:
Figure 3F:
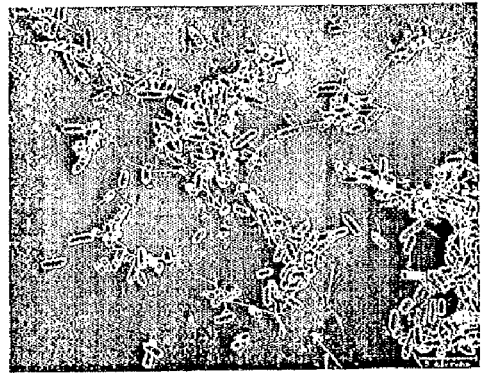
Figures 3G, 3H, 3I:
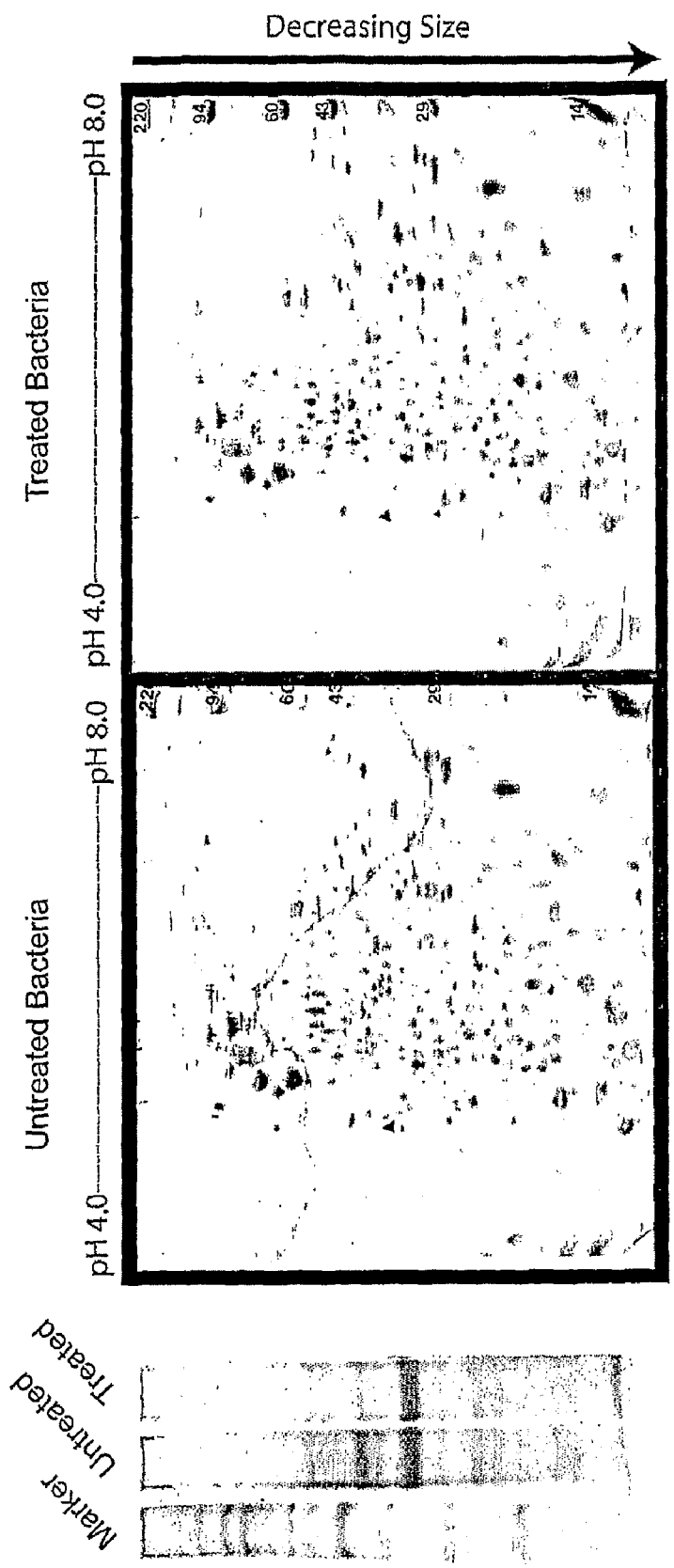

One presently preferred embodiment of an apparatus 10 according to the present invention is depicted in accompanying FIGS. 1 and 2. In this regard, it can be seen that the apparatus includes a standard compressed gas cylinder 12 containing carbon dioxide, and a standard air compressor 14 used in operative association with a carbon dioxide booster 16 (e.g., Haskel Booster AGT 7/30). Alternatively, the air compressor 14 and booster 16 can be replaced with a single carbon dioxide compressor.

An additive cycle is also provided by means of a series of an inlet port 18 which allows additive contained in reservoir 20 to be added to a pressure vessel 22 through valve 24 and additive line 26. The carbon dioxide is introduced to the pressure vessel 22 from header line 27 via valve 28 and $CO_2$ supply line 30. A filter 32 (e.g., a 0.5 micron filter) is provided in the supply line 30 to prevent escape of material from the vessel. A pressure gauge 34 is provided downstream of $CO_2$ shut-off valve 36 in supply header 27 to allow the pressure to be visually monitored. A check valve 38 is provided in the line 27 upstream of the valve 36 to prevent reverse fluid flow into the booster 16. In order to prevent an overpressure condition existing in line 27, a pressure relief valve 9 may be provided.

An outlet line 40 through valve 52 allows the pressure vessel 22 to be depressurized. In this regard, the depressurized fluid exits the vessel 22 via line 40, is filtered by filter unit 42 and then is directed to separator 44 where filtered $CO_2$ gas may be exhausted via line 48, and liquid additive collected via line 50 for possible reuse. Valves 52, 54 may be provided in lines 46 and 27, respectively, to allow fluid isolation of upstream components.

The reactor vessel 22 is most preferably constructed of stainless steel (e.g., 316 gauge stainless steel) and has a total internal volume sufficient to accommodate the organisms being inactivated either on a laboratory or commercial scale. For example, in laboratory studies, an internal volume of 600 mL (e.g., approximately 8 inches long by about 2.5 inches inside diameter) was deemed adequate. As is perhaps more clearly shown in FIG. 2, the pressure vessel 22 includes a vibrator 60, a temperature control unit 62, and a mechanical stirring system most preferably comprised of an impeller 64 and a magnetic driver 66. The reactor vessel 22 contains a conventional basket (not shown) which is also preferably constructed of 316 gauge stainless steel. The basket may be used to support one or more containers holding organisms to be inactivated as well as to protect the impeller 64 and direct the fluid in a predetermined manner.

The reactor vessel 22 may be operated at a constant pressure or under continual pressurization and depressurization (pressure cycling) conditions without material losses due to splashing or turbulence, and without contamination of pressure lines via back diffusion. The valves 24, 28 and 52 allow the vessel 22 to be isolated and removed easily from the other components of the apparatus 10. The top 68 of the pressure vessel 22 may be removed when depressurized to allow access to the vessel's interior.

In use, the organisms to be inactivated are introduced into the interior space of the pressure vessel 22 along with any initial portion of liquid chemical additive from reservoir 20. The temperature control unit 62 is operated so as to set the desired initial temperature for inactivation. The vessel 22 may then be pre-equilibrated with carbon dioxide from gas cylinder 12 at atmospheric pressure, following which the magnetic driver 66 is operated so as to activate the impeller 64. The pressure vessel 22 may thereafter be pressurized to a desired pressure by introducing additional carbon dioxide gas from cylinder 12 via the air compressor 14 linked to booster 16.

In order to effect a pressure cycling of the vessel 22, an amount of carbon dioxide may be released therefrom via depressurization line by momentarily opening valve 52 sufficient to partially reduce pressure within the vessel 22. Additive may be introduced into the vessel 22 for any given pressure cycle by opening valve 24 which allows liquid chemical additive to flow from reservoir 20 into inlet port 18. It will be understood that the chemical additives may be introduced prior to pressurization and/or during pressure cycling. Prior to pressurization, chemical additives may be introduced directly into the reactor vessel 22 prior to sealing and/or via the additive port 18. The chemical additives are most preferably introduced during the cycling stages by measured addition to the additive port 18 at ambient pressures. The port 18 is subsequently sealed and the additive chamber is pressurized so that the additive may enter the reactor vessel 22 without altering the internal pressure. The exact mechanism of addition may be modified such that the process is more efficient and/or convenient.

Following additive introduction, the vessel 22 may be repressurized to a desired pressure following introduction of the liquid chemical additive therein. Such depressurization/repressurization with introduction of liquid chemical additive may be repeated for any number of cycles that may be desired. The cycle of depressurization and repressurization as well as the introduction of the carbon dioxide and liquid chemical additive may be automatically controlled via a controller (not shown) which sequences the various valves discussed previously so as to achieve the desired pressure conditions and cycles.

Most preferably, periodic agitation to the contents of vessel 22 is effected using vibrator 60 through the entire process. Intermittent or continuous agitation of the reactor vessel and its contents is performed by vibrating the reactor vessel during inactivation. Agitation enhances mass transfer of the carbon dioxide and additives by eliminating voids in the fluid such that the organism being inactivated comes into more complete contact with the fluid. The specific means of agitation may be adjusted to accommodate the particular apparatus employed and to optimize the conditions for inactivation (e.g., times, temperatures, pressures, number of cycles). When processing is complete, the vessel 22 is depressurized, the magnetic drive 66 is stopped thereby stopping the stirring impeller 64, and the thus inactivate whole organisms removed by opening top 68 of vessel 22.

Although the precise mechanism by which the present invention enhances inactivation is not entirely understood at this time, it is theorized that, in conjunction with near-critical or supercritical carbon dioxide, the one or more optional chemical additives used in the present invention likely enhance inactivation by increasing the acidity of the interior of the cell, especially in the presence of water. Moreover, chemical additives may enhance the permeability of the cell to carbon dioxide, irreversibly inhibit essential cellular processes, and/or extract components required for cell viability, all of which could possibly contribute to enhancements in inactivation that have been observed.

The present invention will be further understood after careful consideration is given to the following Examples.

EXAMPLE 1

Comparative

The effects of using an additive in accordance with the present invention was compared using the process described by U.S. Pat. No. 6,149,864 to Dillow et al. for inactivating *B. stearothermophilus* spores. Specifically, the most extreme conditions as disclosed in the Dillow '864 patent were evaluated (i.e., three cycles of 60° C. for two hours) and resulted in only 1.0-log inactivation (i.e., $2.3 \times 10^6$ CFU/mL to $2.1 \times 10^5$ CFU/mL) when no chemical additive was used (i.e., 1500 psi to 3000 psi with random agitation). In contrast, 6.4-log inactivation (i.e., $2.3 \times 10^6$ CFU/mL to undetectable) was achieved using the process of the present invention (i.e., 1100 psi to 3000 psi with random and directional agitation, and including TFA as the chemical additive). The chemical additive was placed on a cotton ball and inserted in the chamber prior to closure. No further chemical additive was used.

EXAMPLE 2

Invention

The apparatus generally depicted in FIG. 1 was employed. A sample of *B. stearothermophilus* spores (1 mL) of greater than $10^6$ CFU/mL was placed in 16 mm diameter test tubes in a stainless steel basket. Trifluoroacetic acid (4 mL) was transferred by syringe onto the surface of a cotton ball placed in the basket and water (6 mL) was placed at bottom of vessel. The basket was then loaded into the 600 mL reactor vessel. The reactor vessel was heated to 50° C. and equilibrated with $CO_2$ at atmospheric pressure. The stirring and agitation mechanisms were activated and the reactor vessel pressurized to 2000 psi for 40 minutes. The $CO_2$ pressure was then allowed to drop to 1100 psi at a rate of 300 psi/minute. Agitation by means of vibration of the vessel was carried out for 1 minute.

The pressurization/stirring/agitation/depressurization process was repeated a total of three times. After the third cycle, a series of three flushing cycles to remove the additive was performed by pressurizing and partial depressurizing the reactor vessel using $CO_2$. The stirring was stopped and the basket was removed from the reactor vessel. Any remaining CFU were counted after serial dilution and culturing of both treated and untreated controls.

Complete kill of bioindicators were achieved under different conditions. These reductions correspond to a log reduction in CFU of between 6.2 to 6.9.

EXAMPLE 3A

Invention

A sample of *B. subtilis* spore and vegetative forms (1 mL) of greater than $10^6$ CFU/mL was placed in a 16 mm diameter test tube in a stainless steel basket. Acetic acid (6 mL) was transferred by syringe onto the surface of a cotton ball placed in the basket, which was then loaded into the 600 mL reactor vessel. The reactor vessel was heated to 50° C. and equilibrated with $CO_2$ at atmospheric pressure. The stirring and agitation mechanisms were activated and the reactor vessel pressurized to 3000 psi for 40 minutes. The $CO_2$ pressure was then allowed to drop to 1500 psi at a rate of 300 psi/minute. Agitation was carried out for 1 minute.

After depressurizing the reactor vessel, more acetic acid (4 mL) was introduced at ambient pressure to the additive loop via port 18 (FIG. 1). The loop was sealed and pressurized to 3000 psi. The reactor vessel was the re-pressurized through the additive loop to 3000 psi such that acetic acid was transported into the reactor vessel.

The pressurization/stirring/agitation/depressurization/chemical addition cycle was repeated a total of three times. After the third cycle, a series of three flushing cycles to remove the additive was performed by pressurizing and depressurizing the reactor vessel using $CO_2$. The stirring was stopped and the basket was removed from the reactor vessel. Any remaining CFU were counted after serial dilution and culturing of both treated and untreated controls.

A log reduction in CFU of between 6.0 to 6.9 was observed under different conditions using the process described above.

EXAMPLE 3B

Invention

Example 3A was repeated except that samples containing less than $10^6$ CFU/ml of *B. subtilis* was used. The process resulted in total kill of the *B. subtilis* present. It can therefore be extrapolated from this example that, had greater than $10^6$ CFU/ml of *B. subtilis* been presented, the process would have resulted in a corresponding 6-log reduction in CFU.

EXAMPLE 3C

Comparative

Example 3A was repeated except that the acetic acid was added only once at the beginning of the process. Although a 6-log reduction in CFU was not observed, relatively high log reductions of between 4.5 and 4.7 were observed. This data suggests that multiple additions of acetic acid would be needed in order to achieve the desired 6-log reduction in *B. subtilis* CFU.

EXAMPLE 3D

Invention

Example 3A was repeated except that pressure was maintained at a constant 2000 psi rather than cycling. Compete kill of bioindicators was observed under different conditions. These log reductions in CFU ranged from 6.0 to 7.2.

EXAMPLE 4A

Invention

Example 3D was repeated except that peracetic acid was used as the chemical additive. A log reduction in CFU of between 6.5 to 7.2 was observed under different conditions using the process described above.

EXAMPLE 4B

Invention

Example 4A was repeated except that pressure was maintained at a constant 2000 psi rather than cycling. Complete kill of bioindicators was observed over multiple tests with log reductions in CFU ranging from 6.0 to 7.2.

EXAMPLE 5

Comparative

Example 3A was repeated except that different chemical additives were used under the conditions stated. The results appear in Table 2.

TABLE 2

Comparison of Inactivation by Various Chemical Additives

| Additive | Temp ° C. | Time | Quantity (vol. %) | Cycles | Log Reduction |
|---|---|---|---|---|---|
| HOCl | 60 | 3 hours | 1.0 | 4 | 0-0.50 |
| Ethanol | 50-60 | 3 hours | 1.0 | 4 | 1.2-4.0 |
| Yeast Extract | 60 | 2 hours | 1.0 | 3 | 0.37-1.1 |
| 50% Citric acid | 60 | 2 hours | 1.0 | 3 | 0.03-0.62 |
| Succinic acid | 50 | 2 hours | 1.0 | 3 | 0.25-0.29 |
| Phosphoric acid | 50 | 2 hours | 1.0 | 3 | 0.18-0.25 |
| Formic acid | 50 | 2 hours | 1.0 | 3 | 0 |
| Malonic acid | 50 | 2 hours | 1.0 | 3 | 0-0.12 |

None of the additives evaluated above were effective in achieving at least a 6-log reduction in CFU of *B. stearothermophilus* spores.

EXAMPLE 6

Inactivation of Bacteria by Supercritical Carbon Dioxide

Maintaining the natural presentation environment for a given antigen generally enhances the protective qualities of a given vaccine. Ghost vaccine preparations result in empty bacterial shells that are intact except for holes produced by the lysis gene product when viewed by scanning electron microscopy (SEM) [5, 13, 14]. In contrast, organisms inactivated by supercritical carbon dioxide have intact cell walls (i.e., no lysis holes) and are not empty (i.e., the cytosolic contents are retained). *Staphylococcus aureus* and *Pseudomonas aeruginosa* were inactivated by at least 6-log with supercritical carbon dioxide at 40° C. and 2973 psi to 1500 psi for a total of six cycles over 4 hours. *Escherichia coli* was inactivated by at least 6-log with supercritical carbon dioxide at 34° C. and 2973 psi to 1500 psi for a total of three cycles over 0.5 hours.

EXAMPLE 7

Inactivation of *B. subtilis* and Protein Analysis

A sample of *Bacillus subtilis* (1 mL) spore and vegetative forms of greater than $10^6$ CFU/mL was placed into 16 mm test tubes in a stainless steel basket. Acetic acid (6 mL) was transferred by syringe onto the surface of a cotton ball placed in basket, and the basket then loaded into the 600 mL reactor vessel. The reactor vessel was heated to 50° C. and equilibrated with $CO_2$ at atmospheric pressure. The stirring and agitation mechanisms were activated and vessel pressurized to 3000 psi for 40 minutes. Agitation was carried out for 5 minutes. The $CO_2$ pressure was then allowed to drop to 1500 psi at a rate of 300 psi/minute.

Once the vessel was de-pressurized, 4 mL acetic acid was added at ambient pressure to the additive loop. The additive loop was sealed and pressurized to 3000 psi. The vessel was then repressurized through the additive loop to 3000 psi such that acetic acid was carried into the vessel.

The pressurization/stirring/agitation/depressurization/ chemical addition cycle was repeated a total of three times. After the third cycle, a series of three flushing cycles to remove the chemical additive was performed by pressurizing and de-pressurizing the reactor vessel using $CO_2$. The stirring was stopped and the basket was removed from the vessel. Quantitative analysis of any remaining *B. subtilis* in treated sample vs. untreated control was enumerated though serial dilutions and colony counts. This analysis revealed that total inactivation of the bacterial preparation was achieved (i.e., at least 6-log reduction).

Inactivation was evaluated by performing SEM analysis and protein profiling. Specifically, it was observed that cell walls remained intact. Moreover, extracts of *B. subtilis* spores both untreated and treated with supercritical carbon dioxide were found to be virtually identical. There appeared to have been no substantial loss of antigen from the bacteria as total protein levels were similar.

EXAMPLE 8

Inactivation of *S. typhimurium* and Protein Analysis

A sample of *Salmonella typhimurium* (5 mL), the causative agent for typhoid fever in humans, of greater than $10^9$ CFU/mL was placed into 16 mm test tubes in a stainless steel basket. Water was added on a cotton ball to the vessel at 1% of the total volume (1 vol. %) of the vessel. No chemical additive was placed in the vessel. The reactor vessel was heated to 35° C. and equilibrated with $CO_2$ at atmospheric pressure. The stirring and agitation mechanisms were activated and vessel pressurized to 1500 psi and held constant for 15 minutes. The vessel was then depressurized and the contents removed for analysis. Quantitative analysis of any remaining *Salmonella typhimurium* in treated sample vs. untreated control was enumerated though serial dilutions and colony counts. This analysis revealed that total inactivation of the bacterial preparation was achieved after 15 minutes (i.e., 9-log reduction).

Inactivation was evaluated by performing SEM analysis and protein profiling. Specifically, comparative SEM analysis of untreated bacteria (FIGS. 3A-3C) and treated bacteria (FIGS. 3D-3F) revealed that cell walls remain intact after inactivation. Moreover, protein extracts of untreated and treated bacteria were found to be virtually identical after separation by denaturing sodium dodecyl sulfate (SDS) polyacrylamide gel electrophoresis (FIG. 3G). In addition, there appeared to have been no substantial loss of antigen from the inactivated bacteria as total protein levels are similar. Higher resolution protein analysis was carried out using two-dimensional electrophoresis (FIGS. 3H-3I). This further demonstrated that there was no significant difference between the protein profiles of treated and untreated bacteria. Most antigens do not appear to have been denatured because native polyacrylamide gel electrophoresis during isoelectric focusing resulted in similar migration patterns.

EXAMPLE 9

Immunization with Inactivated *Salmonella typhimurium*

BALB/c mice will be used as subjects for immunization because they are susceptible to *S. typhimurium* infection and the $LD_{50}$ for challenge can be compared with and without vaccination. Immune responses will be measured against both homologous and heterologous whole cells and specific for *Salmonella* lipopolysaccharide (LPS). An initial cohort of 136 BALB/c mice will be inoculated intraperitoneally with equal doses of immunogenic preparations inactivated by supercritical carbon dioxide or mock inoculation (64 mice and 72 control mice).

Three different assays will be performed over the course of the 12 weeks post inoculation. Immune response assays will be performed using pooled sera collected from five different mice each week for 12 weeks as well as pooled pre-inoculation sera from 10 mice.

Total anti-*Salmonella* antibodies will be measured using standard agglutination assays with homologous *S. typhimurium* serotype O4,5. Assays will also be performed using heterologous *S. enteritidis* serotype O9 to test for any significant cross-reactivity indicative of broad protective properties of the vaccine preparations. The results of agglutination assays will be confirmed using a whole-cell ELISA assay for either *S. typhimurium* or *S. enteritidis.*

Humoral responses against LPS have been shown to be a major factor in predicting the protective properties of *Salmonella* vaccines. Of particular importance is the anti-LPS IgG2a subclass. Titers of serum IgA, IgG, IgG1, IgG2a, and IgG2b will be determined by ELISA using *S. typhimurium* LPS antigen. Each of the Ig classes and subclasses will be assayed using the appropriate goat anti-mouse biotinylated antibodies and streptavidin-conjugated horseradish peroxidase. Special note will be made of differences in Ig classes, magnitude of the immune response, duration of immune response, and cross-reactivity with heterologous serotypes.

Eight mice in each cohort will be lightly anaesthetized and then intragastrically infected with 0.2 mL of 10 fold dilutions starting at $5\times10^{10}$ CFU/mL in phosphate-buffered saline (PBS). Carrier only (1× PBS) will be administered in similar fashion to mice serving as negative controls. Mortality will be monitored over a 30 day period using standard protocols and $LD_{50}$ calculations will be determined. Protection will be enumerated as the log 10 increase in $LD_{50}$ of immunized versus control mice. A minimum number of mice will be used consistent with obtaining a statistically significant measurement of antibody response or lack of response to an immunogen.

Thus, experiments to date support the likelihood that bacteria inactivated by supercritical carbon dioxide have potential as high quality whole-cell vaccine preparations. This is supported by the observation that significant log reductions in CFU are achieved for a wide range of bacteria while the morphology of bacteria remains intact, proteins are not significantly degraded, biodegradable polymers are unaffected, and the process is easily scaled up.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the present invention.

REFERENCES

1. Dillow, A. K., et al. (1999) Bacterial inactivation by using near- and supercritical carbon dioxide. Proc. Natl. Acad. Sci. U.S.A. 96:10344-10348.
2. Duque, H., et al. (1989) Effects of formalin inactivation on bovine herpes virus-1 glycoproteins and antibody response elicited by formalin-inactivated vaccines in rabbits. Vaccine 7:513-520.

3. Huter, V., et al. (2000) Improved protection against lung colonization by *Actinobacillus pleuropneumoniae* ghosts: Characterization of a genetically inactivated vaccine. J. Biotechnol. 83:161-172.
4. Murphy, B. R. and Walsh, E. E. (1988) Formalin-inactivated respiratory syncytial virus vaccine induces antibodies to the fusion glycoprotein that are deficient in fusion-inhibiting activity. J. Clin. Microbiol. 26:1595-1597.
5. Jalava, K., et al. (2002) Bacterial ghosts as vaccine candidates for veterinary applications. J. Control. Release 85:17-25.
6. Witte, A., et al. (1990) Phi X174 protein E-mediated lysis of *Escherichia coli*. Biochimie 72:191-200.
7. Eko, F. O., et al. (2000) Characterization and immunogenicity of *Vibrio cholerae* ghosts expressing toxin-coregulated pili. J. Biotechnol. 83:115-123.
8. Eko, F. O., et al. (1994) Immunogenicity of *Vibrio cholerae* ghosts following intraperitoneal immunization of mice. Vaccine 12:1330-1334.
9. Furst-Ladani, S., et al. (1999) Bacterial cell envelopes (ghosts) but not S-layers activate human endothelial cells (HUVECs) through sCD14 and LBP mechanism. Vaccine 18:440-448.
10. Haslberger, A. G., et al. (2000) Activation, stimulation and uptake of bacterial ghosts in antigen presenting cells. J. Biotechnol. 83:57-66.
11. Szostak, M. P., et al. (1996) Bacterial ghosts: Non-living candidate vaccines. J. Biotechnol. 44:161-170.
12. Eko, F. O., et al. (1999) New strategies for combination vaccines based on the extended recombinant bacterial ghost system. Vaccine 17:1643-1649.
13. Huter, V., et al. (1999) Bacterial ghosts as drug carrier and targeting vehicles. J. Control. Release 61:51-63.
14. Lubitz, W., et al. (1999) Extended recombinant bacterial ghost system. J. Biotechnol. 73:261-273.
15. Szostak, M. P., et al., Bacterial ghosts as multifunctional vaccine particles. Behring Institute Mitteilungen, 1997(98): p. 191-6.
16. Eko, F. O., et al. (1994) Production of *Vibrio cholerae* ghosts (VCG) by expression of a cloned phage lysis gene: Potential for vaccine development. Vaccine 12:1231-1237.
17. Mader, H. J., et al. (1997) Endotoxicity does not limit the use of bacterial ghosts as candidate vaccines. Vaccine 15:195-202.
18. Lubitz, W. (2001) Bacterial ghosts as carrier and targeting systems. Expert Opin. Biol. Ther. 1:765-771.
19. Remaut, E., et al. (1983) Improved plasmid vectors with a thermoinducible expression and temperature-regulated runaway replication. Gene 22:103-113.
20. Blasi, U., et al. (1985) Lysis of *Escherichia coli* by cloned phi X174 gene E depends on its expression. J. Gen. Microbiol. 131:1107-1114.
21. Fitzgerald, J. R., et al. (2001) Evolutionary genomics of *Staphylococcus aureus:* Insights into the origin of methicillin-resistant strains and the toxic shock syndrome epidemic. Proc. Natl. Acad. Sci. U.S.A. 98:8821-8826.
22. Ge, Y., et al. (2002) Extraction of natural vitamin E from wheat germ by supercritical carbon dioxide. J. Agric. Food Chem. 50:685-689.
23. Wu, Q. and Marshall, W. D. (2001) Approaches to the remediation of a polychlorinated biphenyl (PCB) contaminated soil—A laboratory study. J. Environ. Monit. 3:281-287.
24. Fages, J., et al. (1994) Use of supercritical $CO_2$ for bone delipidation. Biomaterials 15:650-656.
25. Subramaniam, B., et al. (1997) Pharmaceutical processing with supercritical carbon dioxide. J. Pharm. Sci. 86:885-890.
26. Haas, G. J., et al. (1989) Inactivation of microorganisms by carbon dioxide under pressure. J. Food Safety 2:253-265.
27. Spilimbergo, S., et al. (2002) Microbial inactivation by high-pressure. J. Supercritical Fluids 22:55-63.
28. Fages, J., et al. (1998) Viral inactivation of human bone tissue using supercritical fluid extraction. ASAIO J. 44:289-293.

The entire contents of the above cited references are hereby incorporated by reference.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method of immunization, wherein said method comprises administering to a subject in need thereof an immunogenic preparation of whole microorganisms, wherein said preparation is comprised of whole microorganisms inactivated by at least a factor of $10^6$ with carbon dioxide at or near its supercritical pressure and temperature conditions and a chemical additive wherein the chemical additive is at least one selected from the group consisting of hydrogen peroxide, acetic acid, peracetic acid, and trifluoroacetic acid or mixture thereof.

2. The method of claim 1, wherein said preparation is further comprised of an adjuvant.

3. The method of claim 2, wherein said adjuvant is selected from the group consisting of aluminum or calcium gels, bacterial toxins, cytokines, genes encoding cytokines, muramyl peptides, and saponins.

4. The method of claim 1, wherein said subject is further administered one or more antibiotics and/or antibodies.

* * * * *